United States Patent [19]

Flachslaender et al.

[11] Patent Number: 4,971,063

[45] Date of Patent: Nov. 20, 1990

[54] BLOOD PRESSURE MONITOR AND PNEUMATIC CONNECTOR THEREFOR

[75] Inventors: Erwin Flachslaender, Boeblingen; Jens-Peter Seher, Stuttgart, both of Fed. Rep. of Germany

[73] Assignee: Hewlett-Packard Company, Palo Alto, Calif.

[21] Appl. No.: 311,322

[22] Filed: Feb. 15, 1989

[30] Foreign Application Priority Data

Feb. 25, 1988 [EP] European Pat. Off. ........ 88102787.4

[51] Int. Cl.⁵ ................................................ A61B 5/02
[52] U.S. Cl. .................................. 128/677; 128/681; 128/682; 128/685
[58] Field of Search .................. 128/672, 677–686; 137/231

[56] References Cited

U.S. PATENT DOCUMENTS

| | | | |
|---|---|---|---|
| 2,704,065 | 3/1955 | Clark | 128/685 |
| 3,542,011 | 11/1970 | Langenbeck | 128/681 X |
| 3,738,357 | 6/1973 | Hayes | 128/685 |
| 3,893,478 | 7/1975 | Peters | 128/685 X |
| 4,690,171 | 9/1987 | Johnston | 128/685 X |
| 4,729,382 | 3/1988 | Schaffer et al. | 128/682 X |

FOREIGN PATENT DOCUMENTS 0020110 5/1980 European Pat. Off. .

*Primary Examiner*—Max Hindenburg
*Assistant Examiner*—J. P. Lacyk
*Attorney, Agent, or Firm*—Richard F. Schuette

[57] ABSTRACT

A pneumatic connector for an automated non-invasive blood pressure monitor having a connector body (1) containing two oppositely arranged hollow cavities (8) for insertion of a differential pressure sensor in each cavity. The hollow cavities are connected by a bore (10) which is in connection with the main airway (6,7) in the connector body (1). Additionally, both differential pressure sensors have differential pressure sensors which are connected to the ambient air via a secondary airway.

11 Claims, 4 Drawing Sheets

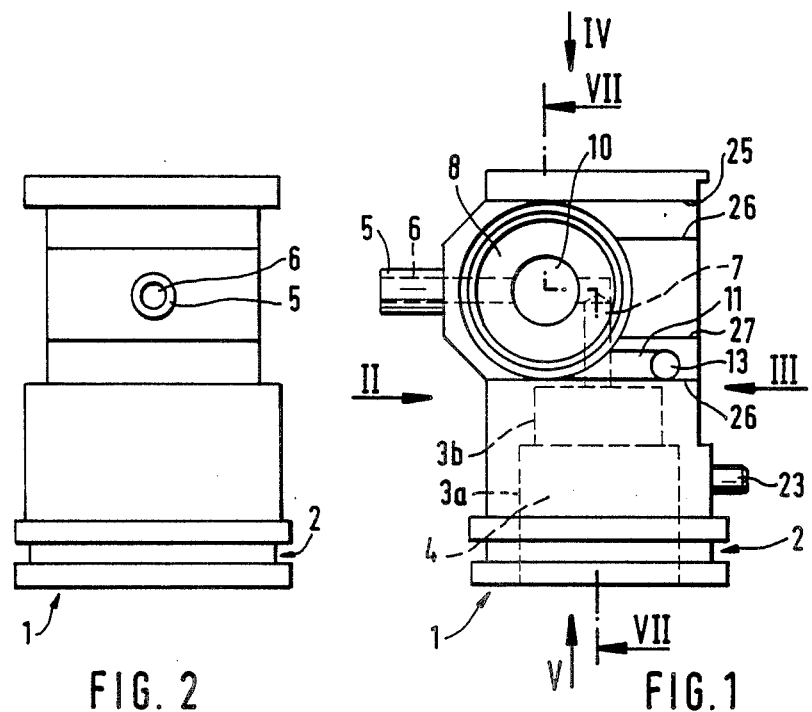
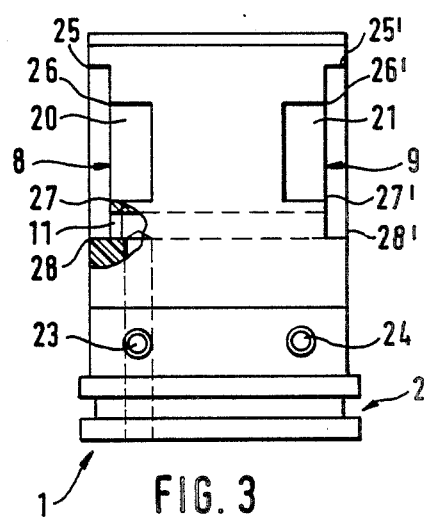
FIG. 2
FIG. 1
FIG. 3

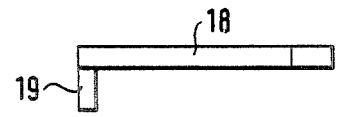
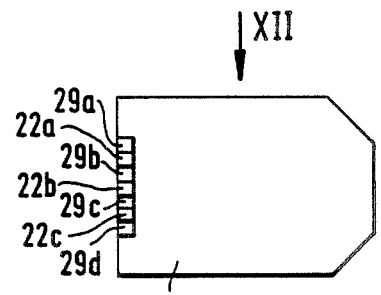
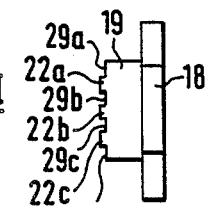
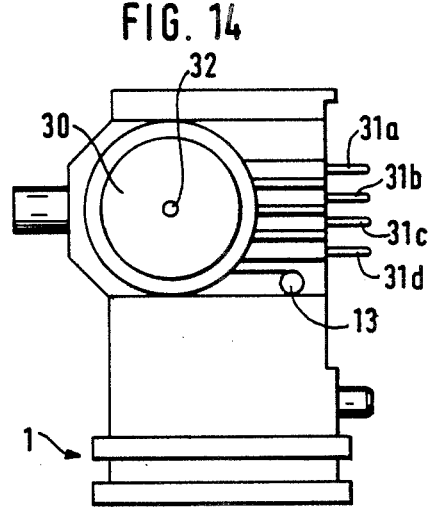
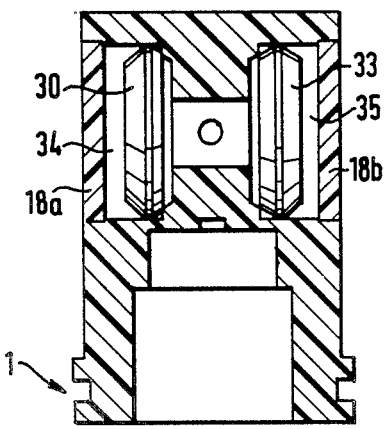

BLOOD PRESSURE MONITOR AND PNEUMATIC CONNECTOR THEREFOR

BACKGROUND OF THE INVENTION

This invention relates to a monitor for the automated non-invasive measurement of a patient's blood pressure comprising means for automatically inflating and deflating a cuff which is to be applied around a patient's extremity, in particular an arm, a pressure sensor coupled to the airway of said cuff and providing an electronic signal indicative of the cuff pressure, electronic means for calculating the blood pressure from the signals obtained by said pressure sensor, in particular from the oscillations of the pressure signal, pneumatic connecting means attached to said monitor—preferably, the casing thereof—said pneumatic connecting means being provided for connection with a cuff connector and comprising a connector body.

Monitors for the automated non-invasive measurement of blood pressure generally comprise a cuff which is to be applied around a patient's arm or leg. This cuff is inflated in periodic intervals by a pressure pump integrated in the monitor. Subsequent to each inflating of the cuff, it is deflated slowly by means of at least one valve integrated in the monitor.

The deflating process is used to determine the blood pressure of the patient, e.g. the systolic, diastolic or mean blood pressure. This can be achieved, for example, by using a microphone which records the Korotkoff sounds which appear when the arteries open (this method is similar to the manual "auscultation" technique). Another method which is better suited for automated blood pressure recordings is the so-called "oscillometric method". According to this method, the oscillations superimposing the generally decreasing cuff pressure are monitored during the deflating process to determine the various blood pressures (systolic, diastolic or mean). The algorithms used to determine the blood pressure from these oscillations are rather complex; algorithms of this kind have been described in a lot of patent applications. An example out of many other ones is European patent application EP-A-208 520.

Monitors of the kind described above comprise a pneumatic connector, usually of the female type, which is attached to the casing of the monitor. In operation, a second (male) pneumatic connector is inserted in the female connector. The second (male) connector is connected with the cuff by means of a flexible tube. Such a monitor further comprises a pressure sensor coupled to the airway of said cuff and providing an electronic signal indicative of the cuff pressure. Such a pressure sensor is necessary for controlling and monitoring the pressure in the cuff, in particular for monitoring the maximum cuff pressure (i.e. the pressure at maximum inflation—this pressure is not identical to the pressure upon which a safety valve may open!) and for controlling the process of cuff deflation (this is particularly important if the cuff is deflated in single decrementing steps). When using the osillometric method which apparently becomes the most common one in the automated monitoring field, the pressure sensor is further required to record the high-frequency oscillations during the deflating process. Such a pressure sensor or pressure transducer is, for example, shown in EP-A-208 520, cf. reference number 105.

Monitors according to the state of the art comprise a lot of airway tubes, T-connectors and tube nozzles arranged inside the monitor. These connection elements are necessary to connect the pump, one or two valves and one or two pressure sensors to the main airway leading to the pneumatic connector at the front end of the monitor. In these monitors, the pressure sensor is arranged inside the monitor casing, and most commonly it is soldered on a printed circuit board. A tube connects the pressure sensor with the pneumatic connector. Such an arrangement has a lot of disadvantages with respect to manufacturing; in particular, the various tubing elements are expensive and time-consuming to assemble. Furthermore, the tubing elements and the pressure sensors mounted directly on the printed circuit board require a lot of space, particularly board space. Other disadvantages do have physical reasons; in particular, the pressure sensor is positioned relatively distant to the patient, and therefore the pressure recorded by the sensor may not correspond to the actual pressure in the cuff as each tube acts as a pressure resistance. Further, the connection tube may expand, and the volume of the airway system is rather large.

It is therefore a major objective of the present invention to provide a monitor for the automated non-invasive measurement of blood pressure which ensures that the actual cuff pressure is recorded very precisely and which is easy and cost-saving to assemble.

BRIEF SUMMARY OF THE INVENTION

According to one aspect of the invention, this objective is solved in a monitor of the type described above by the following features:

The connector body of the pneumatic connecting means comprises at least one hollow cavity adapted to receive the pressure sensor, the hollow cavity is pneumatically connected with the airway of the connecting means, and the pressure sensor is fixed in said hollow cavity in pressure-tight manner.

The connector body itself is preferably manufactured from plastic. The pressure sensor is integrated in said connector body by placing it in a hollow cavity (preferably, a cylindrical bore). The sensor is fixed in said hollow cavity in pressure-tight manner. Such a pressure-tight seat may advantageously be achieved by gluing the pressure sensor in the hollow cavity; a preferred glue ensuring pressure-tightness is a one-component polyester glue.

The hollow cavity is further connected pneumatically with the (main) airway in the pneumatic connector, i.e. the airway leading from a tube nozzle (which is provided for connection to the pump and the valve via a tube) to the outside opening.

As—according to the invention—the pressure sensor is integrated in the connector body, the sensor is positioned closer to the cuff than in prior art monitors. Therefore, the cuff pressure may be recorded more precisely. Further, the connector body (whether manufactured from plastics, metal or any other suitable material) contains only well-defined cavities and bores which do not influence the recorded pressure value, whereas—in prior art arrangements—the necessary tubes could expand when pressure was applied to them, and, thus, distort the measured value. By omittance of tubes as required in prior art solutions, the volume of the airway system is reduced. Further, the pressure resistance effect of connector tubes is ommitted.

The solution provided by the present invention has also manufacturing and cost advantages. In particular, costs can be saved as there is no need for tubes, T-connectos and the like (the pneumatic connecting means according to the invention only provides one tube nozzle for connection to the pump and the valve and an outside opening). Manufacturing costs may be saved by the simplified assembly of the new connector. Last not least, the invention helps to save space inside the monitor, particularly board space (space on printed circuit boards).

The invention further relates to a pneumatic connector for attachment to an automated non-invasive blood pressure monitor—preferably, for attachment to the casing thereof—said pneumatic connector being provided for connection with a cuff connector and comprising a connector body. According to this aspect of the invention, the connector body comprises at least one hollow cavity—preferably, a cylindrical bore—adapted to receive a pressure sensor; the hollow cavity is pneumatically connected with the airway of said pnuematic connector, and said pressure sensor is fixed in the hollow cavity in pressure-tight manner.

It has been found that it may be advantageous to use not only one pressure sensor (which is most commonly a piezoelectric sensor), but two independent pressure sensors instead. These two pressure sensors may be used to control each other in order to detect malfunctions. The connector body of the pneumatic connector provides therefore two hollow cavities adapted to receive a pressure sensor each. In this case, it is advantageous if the two hollow cavities are located opposite each other and if they are connected by a bore which is in connection with the airway of the pneumatic connector. Such a connector is not only easy to manufacture (in addition to the other advantages as outlined above), but it also ensures that both pressure sensors receive the same pressure which cannot be guaranteed if they are connected to the connector using tubes.

Most pressure sensors used in the technique of non-invasive blood gas monitoring are differential pressure sensors, i.e. they generate an electrical signal indicative of the difference between the unknown (cuff) pressure to be measured and a reference pressure, usually the pressure of the ambient air. If such a differential pressure sensor is—as in prior art monitors—placed inside the monitor, it is a major problem that the reference input of the sensor is not exposed to the pressure of the room air, but rather to the pressure inside the monitor which may differ from the outside pressure caused e.g. by temperature effects, convection and the like.

According to a preferred embodiment of the invention, the connector body comprises at least one additional bore connecting the reference input of the differential pressure sensor to the outside. This is a very cheap and easy-to-manufacture solution which ensures that the outside pressure is applied to the reference input of the pressure sensor. This solution requires no additional tubes, connecting means therefor etc. to connect the reference input of the differential pressure sensor to the outside.

Advantageously, a cover is used covering the outside of the pressure sensor. This cover defines a reference pressure chamber connecting the reference input of the pressure sensor with the additional bore. This ensures that no further components like bores, tubes etc. are necessary to connect the reference input of the pressure sensor with the outside. In particular, said cover may be fastened to the connector body by a glue or adhesive. The connector body may further provide additional recesses, said cover fitting on these for further sealing. According to a preferred embodiment, said cover comprises recesses for guiding the pins of the pressure sensor and allowing them to project to the outside of the pneumatic connector. These pins may then be directly soldered to a printed circuit board to save additional electrical connections.

If the pneumatic connector comprises two differential pressure sensors, advantageously a common bore connects the reference inputs of said differential pressure sensors, said common bore being connected to the outside by an additional bore approximately perpendicular to said common bore. Such a solution is not only easy to manufacture, but has the additional advantage that the reference inputs of both differential pressure sensors receive exactly the same reference signal via their common bore. The two hollow cavities may be covered by a common, generally U-shaped cover which is preferably glued to the connector body. Such a cover will define two reference pressure chambers connecting the reference inputs of the differential pressure sensors with the common bore. Such a common cover may be positioned very tight to the connector body and is easy to assemble.

According to a further advantageous embodiment, the outside of the connector body is covered by an outside cover which comprises recesses at its back side connecting the outlet of said additional bore with the ambient air. Room air has therefore to pass said recesses to reach the additional bore leading to the one or two differential pressure sensor(s). This ensures that the outside opening of said additional bore cannot be blocked by foreign bodies. Preferably, said recesses connect the outside opening of the additional bore in the connector body with a large opening in the outside cover, said large opening being provided for insertion of the cuff connector. A pneumatic connector embodying the invention will now be described—by way of a non-limiting example—with reference to the accompanying drawings, in which:

BRIEF DESCRIPTION OF THE DRAWINGS

FIG. 1 is a side view of a pneumatic connector embodying the invention,

FIG. 2 is a side view of this connector in the direction of arrow II of FIG. 1,

FIG. 3 is a further side view according to arrow III of FIG. 1,

FIG. 11 is the bottom view of a cover covering one of the pressure sensors, FIG. 12 is a side view of this cover according to arrow XII of FIG. 11, FIG. 13 is a further side view according to arrow XIII of FIG. 11, FIG. 14 depicts a view similar to that of FIG. 1, but including a differential pressure sensor, and FIG. 15 is a cross section similar to that of FIG. 7, but also including the differential pressure sensors.

DETAILED DESCRIPTION OF THE INVENTION

In FIG. 1, the connector body of a pneumatic connector is generally outlined as 1. This connector is intended for attachment to the casing of an automated non-invasive blood pressure monitor. Connector body 1 is snapped in an appropriate opening of the front wall of said casing by means of groove 2. Connector body 1 is manufactured from plastics.

A cuff connector—not shown—is introduced into an opening 4 of connector body 1 during operation. In FIG. 1, the contour of opening 4 is shown by broken lines 3a and 3b; the opening can further be seen in FIG. 7 which is a section along line VII—VII of FIG. 1. The cuff connector is connected via a tube to the cuff which is to be applied around a patient's arm. Connector body 1 is further connected with a pump and at least one valve inside the monitor; for this purpose, connector body 1 provides a tube nozzle 5 for connection with a tube. In operation, the monitor inflates the cuff by applying a pressure generated by a pump (not shown) to tube nozzle 5; a main airway in the connector body defined by a first connection line 6 (in broken lines), a second connection line 7 (also in broken lines) and opening 4 connects tube nozzle 5 with the cuff connector. As the cuff connector is connected with the cuff via a tube, the pump pressure is applied to the cuff and inflates it. When the maximum cuff pressure is achieved, the monitor stops inflating the cuff and starts the deflating process by opening a valve. During the deflating process, the oscillations superimposing the generally decreasing cuff pressure are monitored. These oscillations are indicative of the blood pressure (systolic, diastolic, mean) of the patient. The calculated blood pressure(s) are then monitored or recorded.

Figure 6:
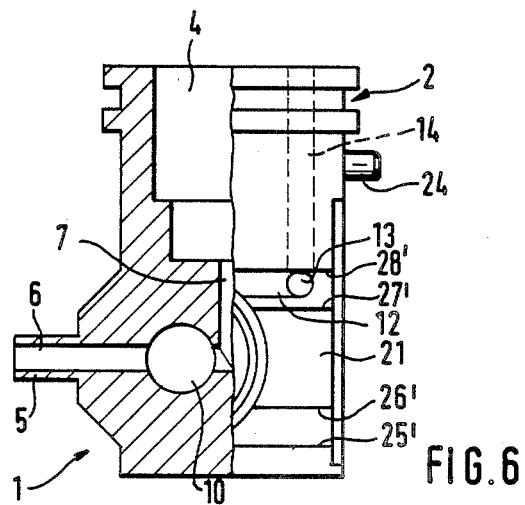
FIG. 6 is the back view of the pneumatic connector according to arrow VI of FIG. 4, the left half of the connector being partially broken away.

The main airway inside the connector body can also be seen in FIG. 6 which is a backside view with the left part partially broken away. The main airway is defined by connection lines 6 and 7 and opening 4.

The connector body further provides two hollow cavities 8 and 9 for insertion of a differential pressure sensor in each cavity. These sensors are required for monitoring the cuff pressure, in particular the maximum cuff pressure and the oscillations caused by the opening of the patient's arteries during the deflating process. For graphical purposes, these sensors are not shown explicitly in FIGS. 1–7; they fit exactly in hollow cavities 8 and 9 and are attached there in pressure-tight manner by a one-component polyester glue. The signal inputs of the differential pressure sensors are connected via a bore 10 which is also in contact to the main airway as defined by connection lines 6 and 7.

Within connector body 1, recesses 11 and 12 (FIGS. 1 and 6) are defined. A cross section of recess 11 can be further seen in the small broken-away region in FIG. 3.

Recesses 11 and 12 are connected via a common bore 13. Said common bore is further in connection with an additional bore 14 which connects common bore 13 with the ambient air. Common bore 13 and additional bore 14 define a secondary airway which is not in connection with the main airway as defined by connection lines 6 and 7 and opening 4. This secondary airway provides connection of the reference inputs of the differential pressure sensors with the ambient air.

Figure 4:
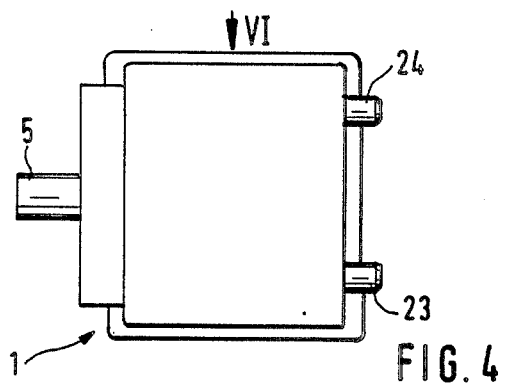
FIG. 4 is the top view according to arrow IV of FIG. 1.
Figure 5:
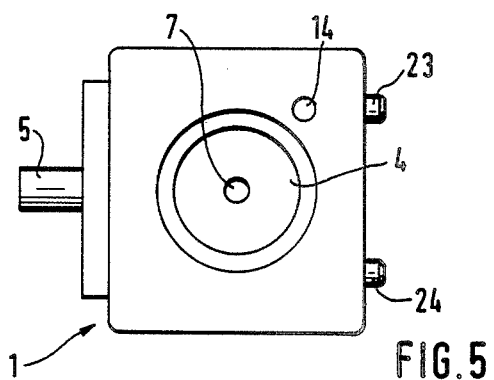
FIG. 5 is the bottom view according to arrow V of FIG. 1.
Figure 8:
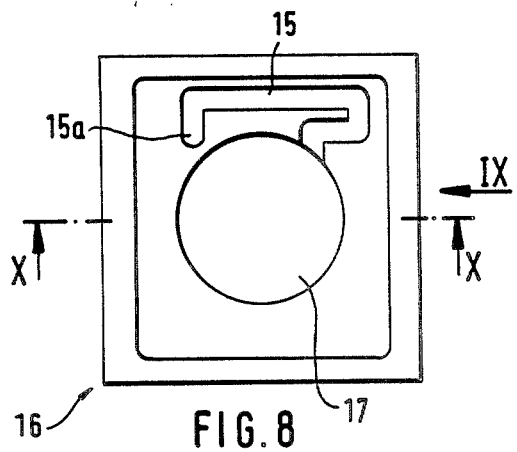
FIG. 8 is the backside view of the outside cover covering the front end of the connector.
Figure 9:
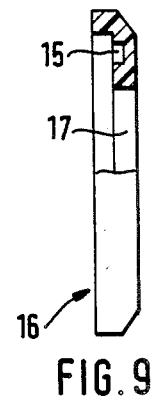
FIG. 9 is a side view of this outside cover according to arrow IX of FIG. 8, the upper part of this cover being partially broken away.
Figure 10:
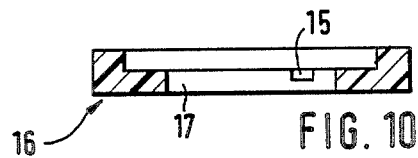
FIG. 10 is a section along line X—X of FIG. 8.

After attachment of the connector body to the casing of the monitor, the outside of the connector body is covered by an outside cover as shown in FIG. 8. FIG. 8 depicts a backside view of said outside cover 16. A recess 15 connects the outside opening of additional bore 14 with the ambient air. For this purpose, outside cover 16 is placed on the front end of connector body 1 (i.e. the bottom side according to FIG. 1) such that the end 15a of recess 15 faces the outside opening of additional bore 14. For example, one could take outside cover 16 as shown in FIG. 8 and turn it around its vertical axis; then it would fit exactly on the connector body front end as shown in FIG. 5.

Outside cover 16 is snapped on a connector body 1. Opening 17 serves for insertion of the cuff connector.

When the differential pressure sensors are placed in hollow cavities 8 and 9, these cavities are further covered each by a cover of the type as depicted in FIG. 11. Such a cover 18 fits exactly over hollow cavities 8 and 9 which contain the differential pressure sensors. Over each of hollow cavities 8 and 9, a cover 18 is placed and glued there. Further, cover 18 fits in recesses of connector body 1 which are defined by edges 23, 23', 24, 24', 25, 25', 26 and 26'. These covers define reference pressure chambers as will be explained by means of FIG. 15.

A projection 19 of cover 18 covers the lower openings 20 and 21 (FIG. 3) adjoining hollow cavities 8 and 9. Portion 19 is equipped with teeth 22a, 22b and 22c. The spaces or recesses 29a, 29b, 29c, 29d between these teeth receive the electrical connection pins of the differential pressure sensor when the pneumatic connector is completely assembled. These pins then project to the outside of the connector. Therefore, the connector may be directly soldered to a printed circuit board; the feet 23 and 24 (FIGS. 1, 3, 4 to 6) seat on the printed circuit board in this case.

Instead of using two covers as depicted in FIG. 11, it is also possible to use a common, generally U-shaped cover to cover cavities 8 and 9; such a common cover may be snapped on connector body 1.

FIG. 14 depicts a side view of connector body 1 similar to that of FIG. 1. A differential pressure sensor 30 fits exactly in the chamber defined by hollow cavity 8 (cf. FIG. 1) and is glued there. Differential pressure sensor 30 provides four pins 31a, 31b, 31c and 31d projecting to the outside. These pins fit into recesses 29a–29d of a cover 18 when this cover is applied to connector body 1. Differential pressure sensor 30 provides a reference input 32. A similar input (the measurement input) is located centrally on the bottom side of the sensor and is in contact with bore 10 (cf. FIG. 1).

Figure 7:
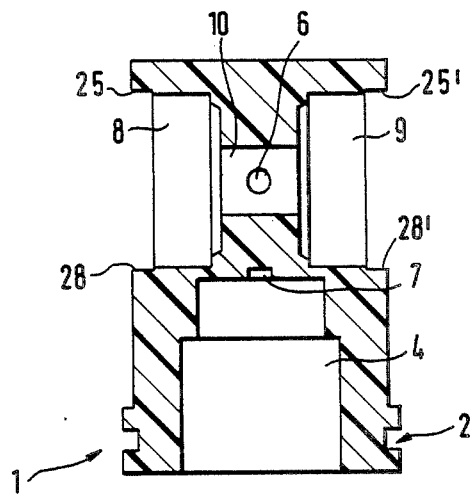
FIG. 7 is a section according to line VII—VII of FIG. 1.

FIG. 15 depicts a cross section of connector body 1 similar to that of FIG. 7. Hollow cavities 8 and 9 (cf. FIG. 7) contain differential pressure sensors 30 and 33. Their outside is covered by covers 18a and 18b which define reference pressure chambers 34 and 35 which connect the reference inputs of pressure sensors 30 and 33 with common bore 13.

We claim:

1. A pneumatic connector for coupling a blood pressure monitor to a blood pressure cuff comprising:
   a connector body, means defining oppositely disposed cavities in outer surfaces of said connector body, said cavities having bottoms facing each other, a first passageway extending between the bottoms of said cavities, a second passageway for receiving air from a pump coupling said first passageway to one point on the surface of said body, a third passageway for connection to a pressure cuff coupling said first passageway to another point on the surface of said body, and pressure sensors respectively mounted to the bottoms of said cavities in a pressure tight manner so that only the bottoms thereof are in communication with said first passageway.

2. A pneumatic connector as set forth in claim 1 wherein said sensors are differential pressure sensors having reference inputs on their sides opposite said bottoms and further comprising:

recesses in outer surfaces of said body respectively leading to the cavities so as to be in communication with said reference inputs, a fourth passageway communicating between said recesses, and a fifth passageway communicating between said fourth passageway and a point on the surface of said body.

3. A pneumatic connector as set forth in claim 2 further comprising:

a U shaped cover extending over said cavities and recesses.

4. A pneumatic connector for coupling a blood pressure monitor to a blood pressure cuff comprising:

a solid body, means defining oppositely disposed cavities in respective outer surfaces of said body, said cavities having bottoms facing each other, a first bore extending between the bottoms of said cavities, a second bore extending from a surface of said body and through said body to said first bore so as to permit air under pressure to be introduced to said bores, a third bore communicating between said first bore and a surface of said body so as to serve as a connection for an airway to a pressure cuff, first and second recesses in outer surfaces of said body respectively communicating with outer portions of said cavities, a fourth bore extending between said first and second recesses, and a fifth bore between said fourth bore and a point on an outer surface of said body.

5. A pneumatic connector as set forth in claim 4 further comprising:

means for covering the said cavities so as to form reference pressure chambers and for covering said first and second recesses.

6. A pneumatic connector as set forth in claim 5 further comprising:

pressure sensors having active sides and reference sides, said sensors being respectively sealed in said cavities with their active sides in communication with said first bore.

7. A pneumatic connector as set forth in claim 6 wherein said pressure sensors have electrical contacts extending therefrom and further comprising:

means defining openings in said covering means through which said contacts extend.

8. A pneumatic connector comprising:

a solid body, means defining a cavity in one side of said body that is adapted to receive a pressure sensor, means defining a first bore inside of said body forming a connection between one point on the surface of the body and said cavity that is adapted to be coupled to a pressure cuff, means defining a second bore in said body forming a connection between said first bore and a point on the surface of said body adapted to be coupled to a source of air, and a pressure sensor having an active side and a reference side mounted in said cavity so that said active side is in sealed communication with said first bore.

9. A connector for coupling a blood pressure monitor to a blood pressure cuff comprising:

a solid body, means defining a cavity in a surface of said body, means defining an opening within said body communicating with said cavity, means defining a first aperture in a surface of said body, said first aperture being adapted for coupling to a tube from a blood pressure cuff, means within said body defining an airway between said opening and said first aperture, means defining a second aperture in a surface of said body, said second aperture being adapted for coupling to a tube from an air pump, means defining a passageway between said second aperture and said opening.

a pressure sensor having an active side and a reference side, said sensor being located within said cavity with its active side facing said opening, and adhesive between said sensor and said means defining said cavity forming a seal between the active and reference sides of said sensor.

10. A connector as set forth in claim 9 further comprising:

means including a cover positioned over said cavity so as to form a reference pressure chamber adjacent to the reference side of said pressure sensor, a third aperture in a surface of said body, and means including means defining a passageway in said body for providing communication between said reference pressure chamber and said third aperture.

11. A connector as set forth in claim 10 further comprising:

electrical connection pins extending from said pressure sensor, and means defining holes in said cover through which said pins respectively pass.

* * * * *